United States Patent
Buchbinder et al.

(10) Patent No.: US 9,914,674 B2
(45) Date of Patent: *Mar. 13, 2018

(54) PROCESS FOR ALKYLATION USING LOW IONIC LIQUID VOLUME FRACTION

(71) Applicant: UOP LLC, Des Plaines, IL (US)

(72) Inventors: Avram M. Buchbinder, Chicago, IL (US); Susie C. Martins, Carol Stream, IL (US); Erin M. Broderick, Arlington Heights, IL (US); Paul T. Barger, Arlington Heights, IL (US); Alakananda Bhattacharyya, Glen Ellyn, IL (US); Douglas A. Nafis, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/675,175

(22) Filed: Mar. 31, 2015

(65) Prior Publication Data

US 2016/0289137 A1    Oct. 6, 2016

(51) Int. Cl.
| | |
|---|---|
| *C07C 2/60* | (2006.01) |
| *C10L 10/10* | (2006.01) |
| *C10L 1/04* | (2006.01) |
| *C10G 29/20* | (2006.01) |
| *C10L 1/06* | (2006.01) |

(52) U.S. Cl.
CPC .............. *C07C 2/60* (2013.01); *C10G 29/205* (2013.01); *C10L 1/06* (2013.01); *C10L 10/10* (2013.01); *C07C 2527/126* (2013.01); *C07C 2531/02* (2013.01); *C10G 2300/305* (2013.01); *C10L 2270/023* (2013.01)

(58) Field of Classification Search
CPC . C07C 2/60; C07C 2527/126; C07C 2531/02; C10L 1/06; C10L 10/10; C10L 2270/023; C10G 29/205; C10G 2300/305

See application file for complete search history.

(56) References Cited

U.S. PATENT DOCUMENTS

| | | | |
|---|---|---|---|
| 7,432,408 B2 | 10/2008 | Timken et al. | |
| 7,432,409 B2 | 10/2008 | Elomari et al. | |
| 7,531,707 B2 | 5/2009 | Harris et al. | |
| 8,183,425 B2 | 5/2012 | Luo et al. | |
| 8,653,318 B2 | 2/2014 | Liu et al. | |
| 8,729,329 B2* | 5/2014 | Hommeltoft | C07C 2/60 585/721 |
| 8,865,960 B2 | 10/2014 | Timken et al. | |

(Continued)

OTHER PUBLICATIONS

Tong et al. ("Surface Tension and Density of Ionic Liquid n-Butylpyridinium Heptachlorodialuminate." Journal of Chemical & Engineering Data 56.10 (2011): 3722-3724).*

(Continued)

*Primary Examiner* — Brian A McCaig
*Assistant Examiner* — Jason Y Chong

(57) ABSTRACT

An alkylation process utilizing less than 10 vol % of a halometallate based ionic liquid catalyst is described. By decreasing the catalyst volume fraction, the level of subsequent undesirable reactions may be minimized. The total residence time is typically in the range of about 1 min to about 30 min. The alkylate typically has a research octane number of at least about 93, and the olefin conversion is typically at least about 96%.

19 Claims, 1 Drawing Sheet

(56) References Cited

U.S. PATENT DOCUMENTS

| | | |
|---|---|---|
| 2004/0133056 A1 | 7/2004 | Liu et al. |
| 2005/0059848 A1 | 3/2005 | Randolph et al. |
| 2007/0142676 A1 | 6/2007 | Elomari et al. |
| 2007/0225538 A1 | 9/2007 | Elomari |
| 2009/0166257 A1 | 7/2009 | Luo et al. |
| 2012/0160740 A1 | 6/2012 | Zhan et al. |
| 2012/0178982 A1 | 7/2012 | Liu et al. |
| 2012/0283500 A1 | 11/2012 | Liu et al. |
| 2013/0345484 A1 | 12/2013 | Martins et al. |
| 2014/0113804 A1 | 4/2014 | Martins et al. |
| 2014/0213435 A1 | 7/2014 | Martins et al. |

OTHER PUBLICATIONS

Han et al.,"Et3NHCl—AlCl3 Ionic Liquids as Catalyst for Alkylation of Toluene . . . ," China Petroleum Processing & Petrochemical Technology (2013), 15(1), 54-60.

Ochedzan-Siodlak et al., "Densities and viscosities of imidazolium and pyridinium chloroaluminate ionic liquids," Journal of Molecular Liquids (2013), v.177, 85-93.

Suxian et al.,"Research on Physical Property of the Et3NHCl/AlCl3 Ionic Liquids," Guangdong Huagong Chemistry (2013), 40(13), 6-7.

Liu et el.,"Reaction Performance of Isobutane Alkylation Catalyzed by a Composite Ionic Liquid . . . ," AlChE Journal (2014), Wiley Library online publication, 1-10.

Wassercheild et al., "Ionic liquids in synthesis," (2008), v.1, Table 3.2-2 & Table 3.2-3.

Okoturo et al., "Temperature dependence of viscosity for room temperature ionic liquids," Journal of Electroanalytical Chemistry (2004), 568, 167-181.

\* cited by examiner

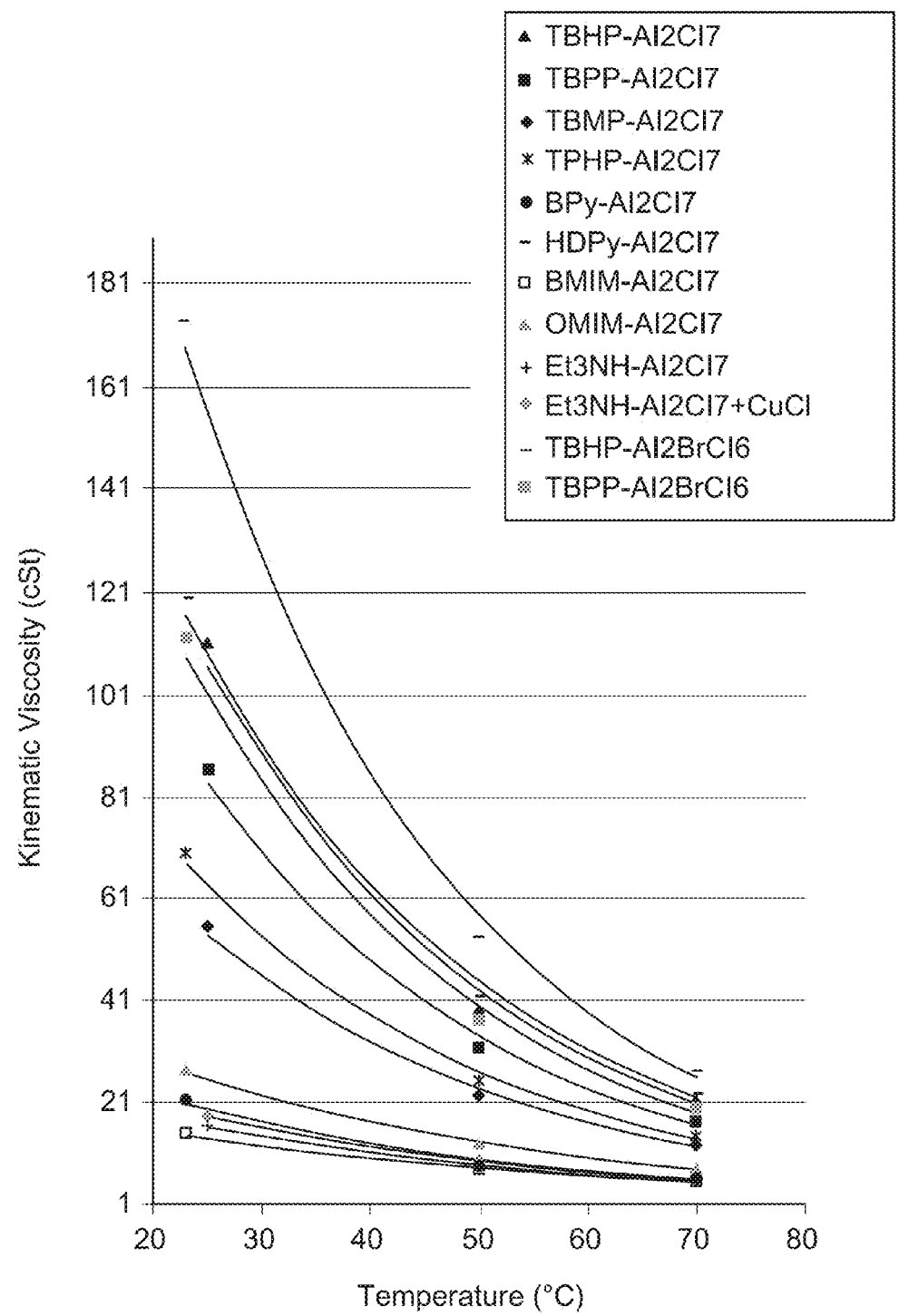

PROCESS FOR ALKYLATION USING LOW IONIC LIQUID VOLUME FRACTION

BACKGROUND OF THE INVENTION

The alkylation of paraffins with olefins for the production of alkylate for gasolines can use a variety of catalysts. The range of suitable process conditions that result in products with high octane and desired selectivity depends on the choice of catalyst.

Ionic liquids are catalysts that can be used in a variety of catalytic reactions, including the alkylation of paraffins with olefins. Ionic liquids are primarily mixtures of salts which melt below about 100° C.

Ionic liquids comprise an organic cation and an anion where the anion is usually an inorganic anion. Ionic liquids are described in U.S. Pat. No. 4,764,440, U.S. Pat. No. 5,104,840, and U.S. Pat. No. 5,824,832 for example. The properties vary extensively for different ionic liquids depending on the cation and the anion. The use of ionic liquids depends on the properties of a given ionic liquid. In addition, the behavior of an ionic liquid may vary considerably for different temperature ranges.

Some alkylation processes utilize low temperatures, typically 10° C. or less, which generally requires chilled cooling fluid for cooling the reactor and/or reactor feeds. This adds substantial cost in the form of additional equipment and energy usage. In some alkylation processes, isoparaffin to olefin (I/O) ratios of 20:1 or greater are used. However, high I/O ratios like these are not desirable from an operating standpoint because they increase the cost of operation, for instance, by requiring larger reactors and more energy for distillation of isoparaffin per unit of alkylate product. Some alkylation processes use ionic liquids having low viscosity (e.g., less than 25 cSt), such as 1-butylpyridinium heptachloroaluminate, 1-butyl-3-methylimidazolium heptachloroaluminate, and triethyl ammonium based ionic liquids. The kinematic viscosity of these ionic liquids was measured in an example herein and determined to be 21.5, 15.0 and 16-19 cSt at 23-25° C. respectively.

U.S. Pat. No. 7,432,408, U.S. Pat. No. 7,432,409, U.S. Pat. No. 7,531,707, and US 2007/0225538 broadly disclose alkylation processes using ammonium, pyridinium, and imidazolium chloroaluminate ionic liquids with I/O ratios in the range of 1 to 100, catalyst volume in the reactor in the range of 2% to 70%, reaction temperatures in the range of −40° C. to 150° C., and residence times of a few seconds to a few hours. However, the Examples use low viscosity (e.g., less than 25 cSt at 25° C.) ionic liquids including 1-butylpyridinium heptachloroaluminate and 1-butyl-3-methylimidazolium heptachloroaluminate. The viscosity of several of the ionic liquids used is unknown, including 1-butyl-4-methylpyridinium heptachloroaluminate, 1-H-pyridinium chloroaluminate, and tributyl-methyl-ammonium chloroaluminate. Based on related ionic liquids, the viscosity of 1-butyl-4-methylpyridinium heptachloroaluminate is believed to be below 40 cSt. In addition, the Examples show an I/O ratio of 4, a temperature of 50° C. for the isopentane and ethylene alkylation. For the isopentane/propylene alkylation and isobutane/isobutene alkylation, an I/O ratio of 8, and a temperature of 10° C. were used. The catalyst volume in the reactor is not stated but can be easily calculated as between 7-8 vol % in U.S. Pat. No. 7,432,408 example 7 which uses propylene as the reactant (at 10° C.). There are no examples for alkylation using propylene or butene at temperatures greater than 10° C., and no discussion of how the process could be improved for higher temperature operation. In the examples for alkylation using butene, the volume of ionic liquid in the reactor is 10-15 vol %.

US 2004/0133056 describes an alkylation process utilizing alkyl-containing ammonium or pyridinium ionic liquid combined with metal compounds of Groups IB and IIB and transition metals. The broad reaction conditions include an I/O ratio of 1:1 or greater, a reaction temperature in the range of −20° C. to 100° C., and a reaction time of 2 sec to 60 min. The ionic liquids used in the Examples were low viscosity (e.g., less than 25 cSt at 25° C.) ionic liquids including triethylammonium chloroaluminates combined with copper chloride, nickel chloride, copper nitrate, and copper sulfate. Most Examples were run at low temperature (less than 10° C.: Ex. 6, 7, 11, 13, 14, 16, and 18) or high I/O ratios (30:1 or more: 10, 12, 13, 14, 16, 17, and 18). The only Examples having I/O ratios of 20:1 or less were run at low temperature (less than 10° C.: Ex. 6, 7, and 11), the reaction products had low $C_8$ content (Ex. 6-9), and/or had low TMP/DMH ratios (Ex. 6-9, 11, and 15). Examples 15, 16, and 17 do not specify the identity or any of the characteristics of the ionic liquid utilized, or its volume fraction in the reactor. Most of the examples used high catalyst volume fraction in the reactor of 14% or greater, with the exceptions of examples 12 (9 vol %) and 14 (4.8 vol %) which used I/O of 200:1 and 150:1 respectively.

US2007/0142676 describes an alkylation process for isopentane and ethylene using pyridinium-based ionic liquids. The broad conditions include a reaction temperature in the range of −20° C. to 200° C., and a reaction time of 0.1 min to 24 hr. The I/O ratio in the example was 3.2, the volume of IL in the reactor was 16%, and the ionic liquid was 1-butylpyridinium heptachloroaluminate.

US 2009/166257 describes an alkylation process utilizing ammonium, pyridinium, and imidazolium chloroaluminate ionic liquids. The broad conditions include an I/O ratio in the range of 1 to 100, a catalyst volume in the reactor of 2% to 70%, a reaction temperature in the range of −40° C. to 150° C., and a residence time of a few seconds to a few hours. The Examples showed a 1-butylpyridinium chloroaluminate ionic liquid, a catalyst volume of 10-15%, and a temperature of 0° C.

US 2012/0178982 describes the alkylation of isobutane and/or isopentane with an olefin having 2 to 8 carbons using an alkyl-containing ammonium, imidazolium, or pyridinium ionic liquid. The I/O ratio is 1:1 or greater, with high I/O ratios being preferred, e.g., at least 20:1, more preferably at least 50:1, even more preferably at least 100:1. The reaction temperature is in the range of −20° C. to 100° C. No examples are given.

US2012/0283500 describes the alkylation of isobutane and butene using alkyl-containing ammonium, imidazolium, or pyridinium ionic liquids. The examples used ionic liquids containing triethylammonium ($Et_3NH$) and 1-butyl-3-methylimidazolium cations, and anions containing chlorohexabromoaluminate or heptachloroaluminate, with some including various copper compounds. The Examples show I/O ratios of 10:1 to 40:1, and temperatures of 20° C. to 30° C. The olefin feed rate for Examples 3-8 and Comparative Examples 1-2 was calculated from the information given to be less than 0.2 g olefin/g ionic liquid/hr (1.4 mol olefin/mol ionic liquid/hr). The olefin feed rate cannot be calculated for Examples 1a-b and 2a-b because no feed rate or olefin feed rate is given for those examples. However, assuming these feed rates were the same as that in Example 4, the olefin feed rate would be less than 0.2 g olefin/g ionic liquid/hr (1.4 mol olefin/mol ionic liquid/hr). In addition, no volume fraction of ionic liquid or residence times are given.

In Liu et al, "Reaction Performance of Isobutane Alkylation Catalyzed by a Composite Ionic Liquid at a Short Contact Time" AIChE Journal, vol 60, pp. 2244-2253, the authors demonstrate isobutane/butene alkylation under various conditions using ionic liquids with $Et_3NH$ cations and chloroaluminate anions with copper chloride additive. The lowest I/O tested was 15:1 and resulted in research octane number of less than 90 and $C_8$ selectivity of less than 55%. Furthermore, the authors study the effect of volume % of IL in the reactor at 15° C., 54:1 I/O and 1 min residence time. The range of volume % investigated was 33-60 volume %. They find that with that ionic liquid and with those conditions, TMP/DMH ratio, octane and $C_8$ selectivity is best at above 50 volume %.

US Application Serial Nos. 2013/0345484 and 2014/0113804 teach that certain phosphonium ionic liquids having a kinematic viscosity greater than 50 cSt at 20° C. are preferable because they result in higher octane than do lower viscosity ionic liquids, and that this advantage is larger at higher operating temperatures. However, the olefin was added with a slow flow rate (0.5 g olefin/g ionic liquid/hr or 5.2 mol olefin/mol ionic liquid/hr), leading to long residence times (e.g., about 115-120 min). Such long residence times are not desirable for commercial practice as they would require very large reactors or very small product production rates.

There is a need for an alkylation process utilizing low amounts of ionic liquid.

SUMMARY OF THE INVENTION

One aspect of the invention is an alkylation process. In one embodiment, the alkylation process includes passing an isoparaffin having from 4 to 10 carbon atoms to an alkylation reactor; and passing an olefin having from 3 to 10 carbon atoms to the alkylation reactor. The alkylation reactor contains a halometallate based ionic liquid catalyst for reacting the olefin and isoparaffin to generate an alkylate having a research octane number of at least about 93. The alkylation reactor is operated at reaction conditions comprising an operating temperature greater than about 20° C., a molar ratio of isoparaffin to olefin of less than about 20:1, an overall olefin feed rate of greater than about 30 mol olefin/mol ionic liquid catalyst/hr, a total residence time in a range of about 1 min to about 30 min, and less than about 10 vol % of the halometallate based ionic liquid catalyst.

BRIEF DESCRIPTION OF THE DRAWING

The FIGURE is a graph showing the kinematic viscosity of various ionic liquids at different temperatures.

DETAILED DESCRIPTION OF THE INVENTION

Conventional HF and $H_2SO_4$ alkylation processes operate in an acid continuous mode. However, in ionic liquid alkylation, the catalyst is sufficiently active as to allow, or even necessitate, operation in a hydrocarbon-continuous mode. In the hydrocarbon-continuous mode of operation, the catalyst is recovered by settling ionic liquid droplets out of the hydrocarbon phase. Small droplets of ionic liquid are not settled efficiently, and at least some loss of ionic liquid is expected. This loss of ionic liquid increases the operating cost of the process because of the high cost of the ionic liquid. Since operating with lower overall amounts of ionic liquid may result in fewer overall losses of ionic liquid, operating with low ionic liquid volume fraction is desirable.

In motor fuel alkylation processes utilizing ionic liquids as catalysts, the high viscosity of ionic liquids often results in a mass transfer limitation on the process which slows the primary reaction, leading to both decreased activity and low selectivity to the primary alkylation product. For instance, in processes using isobutane as the isoparaffin and butenes as the olefin, low $C_8$ selectivities result. On the other hand, in low viscosity ionic liquids, the isomerization of high-octane trimethylpentanes (TMP) to dimethylhexanes (DMH) is fast, leading to lower octane than with higher viscosity ionic liquids. Other factors such as acidity and solubility will also have an effect on activity and selectivities. In some cases such as caprolactamium based ionic liquids, reactivity may be high enough that mass transfer limitations are not as significant as in phosphonium ionic liquids of similar viscosity.

The mass transfer limitations for the primary alkylation reaction may be overcome by generating small droplets or utilizing an ionic liquid with high olefin diffusivity. In such cases, the alkylation reaction is fast. However, in order to achieve the desired high octane and $C_8$ selectivity for isobutane and butene alkylation, the subsequent reactions of alkylate need to be minimized. These reactions include the production of light ends ($C_5$-$C_7$ products in isobutane and butene alkylation), heavies ($C_9$ and heavier products), and isomerization of higher octane isomers (TMPs) to lower octane $C_8$ isomers such as DMHs. When residence time is low (for instance, less than about 3 minutes) olefin flow rate must be high in order to produce a low I/O (for instance, residence time less than 3 minutes and I/O of 10). Not wishing to be bound by theory, when the olefin feed rate is high and/or when the ionic liquid is viscous, mass transfer resistance leads to elevated local olefin concentrations which favors increased heavies formation by oligomerization (or by alkylation of reaction intermediates). Selectivity to heavies can generally be reduced by improving mass transfer conditions. One means to achieve lower selectivity to heavies (and higher selectivity to C8s) is by reducing the olefin feed rate. However, if low overall I/O is desired, longer residence time is needed (for instance, residence time longer than about 3 minutes). Longer residence time, in turn, leads more extensive secondary reactions such as undesired isomerization of TMP to DMH resulting in low alkylate octane. Utilizing lower ionic liquid volume fraction reduces the rate of these undesired secondary reactions, resulting in higher octane, $C_8$ selectivity and higher ratio of TMP to DMH.

Higher selectivity is normally achieved at high I/O ratios. This is due to the high concentration of the hydride transfer agent (isobutane) relative to active alkylate product. In acid-continuous systems, such as HF and $H_2SO_4$, this is accomplished by using high local I/O ratios (low local olefin concentration). In an acid-continuous system, unless the diffusivity of hydrocarbons into the acid is very high, changing the volume fraction will not significantly change the amount of accessible acid sites. Even in a case with high hydrocarbon solubility in the acid phase, reducing the acid volume fraction in an acid continuous system has limited effect because the acid fraction can only be decreased to the limit of phase inversion.

However, in a hydrocarbon-continuous process (which is possible with ionic liquid alkylation due to stronger acidity), adjusting the ionic liquid volume fraction significantly changes the catalyst surface area. By decreasing the catalyst volume fraction, the level of subsequent undesirable reactions may be minimized. In some cases in order to do this, the residence time must be lengthened to ensure full olefin conversion.

Due to the low solubility of hydrocarbons in ionic liquids, olefins-isoparaffins alkylation, like most reactions in ionic liquids, is generally biphasic. The catalytic alkylation reaction is generally carried out in a mixed phase liquid-liquid system. The system can be a batch system, a semi-batch system, or a continuous system as is usual for aliphatic alkylation. Vigorous mixing is desirable to ensure good contact between the reactants and the catalyst.

The present invention involves the use of a low volume fraction of ionic liquid catalyst in ways that are advantageous compared to a high volume fraction. Volume fraction is calculated by dividing the total volume of ionic liquid in the reaction zone by the total volume of liquids, solids and supercritical fluids in the reaction zone. Volume percent is volume fraction multiplied by 100. The present invention uses less than 10 vol % ionic liquid relative to the total liquid contents of the reactor. This is desirable for achieving higher selectivity and octane. In most cases, a volume fraction of about 5 vol % or less is preferable, or less than about 4 vol %, or less than about 3 vol %. One aspect of the invention is selecting an ionic liquid with properties high activity and/or low viscosity) that allows the use of an ionic liquid loading of about 2 to about 2.5 vol %. The ionic liquid catalyst volume percent relative to the liquid contents of the reactor is generally in the range of less than about 10 vol %, or less than about 9 vol %, or less than about 8 vol %, or less than about 7 vol %, or less than about 6 vol %, or less than about 5 vol %, or less than about 4 vol %, or less than about 3 vol %, or less than about 2 vol %, or about 0.5 vol % to about 10 vol %, or about 0.5 vol % to about 5 vol %, or about 0.5 vol % to about 4 vol %, or about 0.5 vol % to about 3 vol %, or about 1 vol % to about 5 vol %, or about 1 vol % to about 3 vol %.

For most types of ionic liquids, additional advantage can be obtained if lower viscosity ionic liquids are used. In these cases, lower volume fractions can be utilized because the diffusivity of the reactants is higher. As a result, more of the ionic liquid is utilized, and full conversion in the primary alkylation reaction can be achieved in relatively short time. In some embodiments, the use of a halometallate based ionic liquid that has a viscosity of less than about 120 cSt at a temperature of 25° C. allows the use of less than about 5 vol % of the ionic liquid catalyst. In some embodiments, the halometallate based ionic liquid catalyst has a viscosity of less than about 100 cSt at a temperature of 25° C., and less than about 5 vol % of the ionic liquid catalyst is used. In some embodiments, the halometallate based ionic liquid catalyst has a viscosity of less than about 100 cSt at a temperature of 25° C., and less than about 4 vol % of the ionic liquid catalyst is used. In other embodiments, the use of a halometallate based ionic liquid catalyst having a viscosity of less than about 60 cSt at a temperature of 25° C. allows the use of less than about 3 vol % ionic liquid catalyst.

In some embodiments, longer residence times are needed in order to achieve the desired conversion when using low amounts of ionic liquid. Generally, the residence time is in the range of about 1 min to about 30 min. In some embodiments, when there is less than about 5 vol % of the halometallate based ionic liquid catalyst, the total residence time is in the range of about 2 min to about 10 min. In other embodiments, when there is less than about 4 vol % of the haloaluminate based ionic liquid catalyst, the total residence time is in the range of about 3 min to about 30 min. In other embodiments, when there is less than about 3 vol % of the haloaluminate based ionic liquid catalyst, the total residence time is in the range of about 4 min to about 30 min.

The ionic liquid is a halometallate based ionic liquid. The anionic component generally comprises a halometallate of the form $M_nX_{3n+1}$, where n is from 1 to 5; X is Cl, Br, I, or combinations thereof; and M is Al, Fe, Cu, Ni, or combinations thereof. The ionic liquid mixture can comprise a mix of the halometallates where n is 1 or 2, and includes a small amount of the halometallates with n equal to 3 or greater. In some embodiments, the anionic component of the ionic liquid comprises a haloaluminate. In some embodiments, the anionic component of the ionic liquid comprises a chloroaluminate. In some embodiments the anionic component comprises a heptachloroaluminate. Here, heptachloroaluminate refers to an anion, a group of anions, or anions and aluminum chloride compounds that comprise chlorine atoms and aluminum atoms in a ratio of about 7 to about 2.

The cation of the ionic liquid is typically a phosphonium based ionic liquid, an imidazolium based ionic liquid, a pyridinium based ionic liquid, a pyrrolidinium based ionic liquid, a pyrrolidonium based ionic liquid, or a lactamium based ionic liquid. Suitable cations include, but are not limited to, tripropylpentylphosphonium, tripropylhexylphosphonium, tributylpentylphosphonium, tributylhexylphosphonium, tributylmethylphosphonium, 1-butyl-3-methyl imidizolium, 1-ethyl-3-methylimidazolium, 1-butylpyridinium, 1-ethylpyridinium, 1-butyl-2-methyl-pyridinium, 1-butyl-3-methyl-pyridinium, 1-butyl-4-methyl-pyridinium, 1-ethyl-1-methylpyrrolidinium, 1-butyl-1-methylpyrrolidinium, 1-butyl-1-ethylpyrrolidinium, caprolactamium, N-methylcaprolactamium, N-methylpyrrolidonium, pyrrolidonium, δ-valerolactamium, N-methyl-δ-valerolactamium, or combinations thereof.

Suitable ionic liquids include, but are not limited to, tripropylpentylphosphonium heptachloroaluminate, tripropylhexylphosphonium heptachloroaluminate, tributylpentylphosphonium heptachloroaluminate, tributylhexylphosphonium heptachloroaluminate, tributylmethylphosphonium heptachloroaluminate, 1-butyl-3-methyl imidizolium heptachloroaluminate, 1-ethyl-3-methylimidazolium heptachloroaluminate, 1-butylpyridinium heptachloroaluminate, 1-butyl-2-methyl-pyridinium heptachloroaluminate, 1-butyl-3-methyl-pyridinium heptachloroaluminate, 1-butyl-4-methyl-pyridinium heptachloroaluminate, 1-ethyl-1-methylpyrrolidinium heptachloroaluminate, 1-butyl-1-methylpyrrolidinium heptachloroaluminate, caprolactamium heptachloroaluminate, N-methylcaprolactamium heptachloroaluminate, N-methylpyrrolidonium heptachloroaluminate, pyrrolidonium heptachloroaluminate, δ-valerolactamium heptachloroaluminate, N-methyl-δ-valerolactamium heptachloroaluminate, or combinations thereof.

When water enters the reaction, whether brought in with a feed, or otherwise, there can be a shift, where the haloaluminate forms a hydroxide complex, or instead of $Al_nX_{3n+1}$, $Al_nX_m(OH)_x$ is formed where m+x=3n+1. However, moisture is not desirable. Ionic liquids also present some advantages over other liquid alkylation catalysts, such as being less corrosive to some materials than catalysts like HF, and being non-volatile.

The acidity needs to be controlled to provide for suitable alkylation conditions. In some embodiments, addition of a catalyst promoter, such as a Brønsted acid or a Brønsted acid precursor is employed. Suitable examples of Brønsted acid promoter are HCl or HBr although other Brønsted acids may be employed. Suitable examples of Brønsted acid precursors are haloalkanes which react in the presence of the ionic liquid to form a hydrogen halide and an olefin. For instance, 2-chlorobutane, 2-chloro-2-methylpropane, 2-bromobutane, and 2-bromo-2-methylpropane are suitable promoters. The promoter is employed to enhance the activity of the catalyst by boosting the overall acidity of the ionic liquid-based catalyst. In some embodiments, the molar ratio of olefin to acid promoter of greater than about 15:1, or greater than about 25:1, or greater than about 30:1, or higher. The molar ratio of olefin to acid promoter is defined as the amount of olefin added to the reaction in a given period of time or present at the beginning of the period of time, divided by the amount of acid promoter fed to the reaction in the given period of time or present at the beginning of the period of time.

The isoparaffin and olefin can be introduced separately or as a mixture, in one or multiple locations. The molar ratio of isoparaffin to olefin is generally less than about 20:1, or less than about 15:1, or less than about 13:1, or in the range of about 2:1 to about 20:1, or in the range of about 8:1 to about 12:1.

In a semi-batch system, the catalyst and at least a portion of the isoparaffin are introduced with no olefin present, followed by the olefin or a mixture of isoparaffin and olefin. In a semi-batch system the olefin is added gradually over a period of time. The catalyst is measured in the reactor with respect to the amount of total olefins added over the course of the reaction, with a catalyst to olefin weight ratio between 0.1:1 and 10:1, and preferably between 0.2:1 and 5:1, and more preferably between 0.4:1 and 2.5:1.

In a continuous system, the catalyst, the isoparaffin, the olefin, and optionally the catalyst promoter are each added continuously. Catalyst, optional catalyst promoter, unreacted isoparaffin, and unreacted olefin are each removed continuously from the reaction zone along with alkylate product. The catalyst, catalyst promoter, unreacted isoparaffin, and/or unreacted olefin may be recycled. The olefin may be added to one or more locations in the reaction zone. It is preferable to add the olefin to multiple locations in the reaction zone. Adding olefin in multiple locations, or spreading the olefin addition over a longer period of time results in the isoparaffin to olefin ratio measured in a specific location at a specific point in time to be higher. The isoparaffin to olefin ratio is defined as the cumulative amount of isoparaffin divided by the cumulative amount of olefin added across the entire reaction zone.

The overall olefin feed rate is typically at least about 30 mol olefin/mol ionic liquid/hr, or at least about 35 mol olefin/mol ionic liquid/hr, or at least about 40 mol olefin/mol ionic liquid/hr, or at least about 45 mol olefin/mol ionic liquid/hr, or at least about 50 mol olefin/mol ionic liquid/hr, or at least about 55 mol olefin/mol ionic liquid/hr, or at least about 60 mol olefin/mol ionic liquid/hr, or at least about 75 mol olefin/mol ionic liquid/hr, or at least about 100 mol olefin/mol ionic liquid/hr, or at least about 125 mol olefin/mol ionic liquid/hr, or at least about 150 mol olefin/mol ionic liquid/hr, or at least about 175 mol olefin/mol ionic liquid/hr, or at least about 200 mol olefin/mol ionic liquid/hr, or at least about 225 mol olefin/mol ionic liquid/hr, or at least about 250 mol olefin/mol ionic liquid/hr. In a batch or semi batch process, the moles of ionic liquid is measured as the total amount of ionic liquid in the reactor. In a semi batch process, the moles of olefin per hour is measured as the total molar flow rate of olefin added to the reactor per hour. In a batch process, the moles of olefin per hour is measured as the total moles of olefin added to the reactor divided by the total reaction time. In a continuous process, the olefin feed rate is measured as the total molar flow rate of olefin divided by the total molar flow rate of ionic liquid divided by the overall liquid residence time.

In some embodiments, olefin may be added to several locations in the reaction zone. The overall olefin feed rate is defined as the sum of all olefin flows added to the reaction zone.

Advantageously, the process does not require cooling below environmental temperatures or conditions. The process is operated at temperatures greater than about 20° C. The reaction temperature is generally in the range about 20° C. to about 100° C., or about 20° C. to about 70° C. In some embodiments, the operating temperature is in the range of about 20° C. to about 30° C. In other embodiments, the operating temperature is greater than about 30° C., or in the range about 30° C. to about 100° C., or about 30° C. to about 70° C. The alkylation reaction is exothermic. In some embodiments, the heat of reaction is removed by heat exchange with a cooling fluid. Operation of the reaction at temperatures greater than 30° C. may be desired in order to reduce or eliminate the cost of chilling the cooling fluid.

The pressure can be in the range from atmospheric pressure to 8000 kPa, preferably sufficient to keep the reactants in the liquid phase. For example, when isobutane is used, the pressure is desirably at least about 340 kPa (g) (35 psig) at 20° C. in order to maintain the isobutane in the liquid phase.

The heat generated by the reaction can be removed using any of the methods known to those of skill in the art.

At the reactor outlet, the hydrocarbon phase is separated from the ionic liquid phase by gravity settling based on density differences, or by other separation techniques known to those skilled in the art. Then the hydrocarbons are separated by distillation, and the starting isoparaffin which has not been converted is recycled to the reactor. The catalyst is typically recycled to the reactor as well.

Typical alkylation conditions may include a catalyst volume in the reactor of from about 1 vol % to about 10 vol %, a temperature of from about 20° C. to about 70° C., a pressure of from about 340 kPa(g) to about 5000 kPa(g), an isobutane to olefin molar ratio of from about 2 to about 20, and a total residence time of about 1 min to about 30 min.

In some embodiments, the research octane number of the alkylate is at least about 93, or at least about 94, or at least about 95.

The conversion of the olefin is typically at least about 96%, or at least about 97%, or at least about 98%, or at least about 99%. The percent olefin conversion is defined as (the amount of olefin added to the reactor minus the amount of olefin remaining after the reaction (or at the reactor outlet)) divided by the total amount of olefin added to the reactor times 100. In a continuous process, olefin conversion is defined as (the amount of olefin added to the reactor minus the total flow of olefin out of the reactor) divided by the total flow of olefin into the reactor.

The alkylation process is intended to include the upgrading of lower value hydrocarbons to higher value hydrocarbon products. The preferred alkylation reaction is to react isoparaffins having from 4 to 10 carbon atoms, typically 4 to 5 carbon atoms, more typically 4 carbon atoms, with olefins having from 3 to 10 carbon atoms, typically from 3 to 5 carbon atoms, more typically 4 carbon atoms. The feed streams of isoparaffins and olefins are generally mixtures containing more than one carbon number. For example, an isobutane stream may also contain other paraffins and isoparaffins such as propane, normal butane, isopentane, etc., typically in amounts of less than about 20%. Thus, a stream containing isoparaffins or olefins having 4 carbon atoms will typically contain about 80% or more of isoparaffins or olefins having 4 carbon atoms, and about 20% or less of isoparaffins or olefins having 5 or more carbons or 3 or less carbons.

In some embodiments, the process can be used to upgrade low value $C_4$ hydrocarbons to higher value alkylates. To that extent, one specific embodiment is the alkylation of isobutane with butenes to generate $C_8$ compounds. Preferred products include isomers of trimethylpentane (TMP), namely 2,2,3-trimethylpentane, 2,2,4-trimethylpentane, 2,3,3-trimethylpentane, and 2,3,4-trimethylpentane. Other $C_8$ isomers are also produced. One set of competing isomers are dimethylhexanes (DMH), namely 2,2-dimethylhexane, 2,3-dimethylhexane, 2,4-dimethylhexane, 2,5-dimethylhexane, 3,3-dimethylhexane, and 3,4-dimethylhexane. The quality of the product stream can be measured in the ratio of total TMP to total DMH, with a higher ratio desired, e.g. of greater than about 7:1, or greater than about 10:1, or greater than about 12:1, or greater than about 14:1.

In some embodiments, the alkylation process for butanes and butenes is operated at a temperature greater than about 20° C. In some embodiments, the reaction can have a selectivity for $C_8$ of at least about 65% or more, or at least about 70% or more, or at least about 75% or more. Selectivity for $C_8$ is defined here as the total weight of products containing exactly eight carbon atoms divided by the total weight of products containing five or more carbon atoms. In some embodiments, the alkylate can have a mole ratio of trimethylpentane to dimethylhexane of greater than about 7:1, or greater than about 10:1, or greater than about 12:1 or greater than about 14:1.

In some embodiments, the alkylation process for butanes and butenes is operated at a temperature range of about 20° C. to about 30° C. In some embodiments, the reaction can have a selectivity for $C_8$ of at least about 67% at least about 70% or more, or at least about 75% or more. In some embodiments, the alkylate can have a mole ratio of trimethylpentane to dimethylhexane of greater than about 12:1 or greater than about 14:1. In some embodiments, the alkylate can have a research octane number of at least about 93 or at least about 95 or at least about 96.

In some embodiments, the alkylation process for butanes and butenes is operated at a temperature greater than about 30° C. In some embodiments, the reaction has a selectivity for $C_8$ of at least about 65%. In some embodiments, the alkylate has a mole ratio of trimethylpentane to dimethylhexane of greater than about 7:1.

EXAMPLES

Example 1

Viscosity of Ionic Liquids

Phosphonium based ionic liquids were prepared by methods analogous to those described Example 1 of in US Publication No. 2013/0345484. Other ionic liquids were prepared similarly from appropriate precursors. Tributylhexylphosphonium heptachloroaluminate (TBHP-$Al_2Cl_7$) was prepared from tributylhexylphosphonium chloride with addition of two molar equivalents of $AlCl_3$; tributylpentylphosphonium heptachloroaluminate (TBPP-$Al_2Cl_7$) was prepared from tributylpentylphosphonium chloride with addition of two molar equivalents of $AlCl_3$; tributylmethylphosphonium heptachloroaluminate (TBMP-$Al_2Cl_7$) was prepared from tributylmethylphosphonium chloride with addition of two molar equivalents of $AlCl_3$; tripropylhexylphosphonium heptachloroaluminate (TPHP-$Al_2Cl_7$) was prepared from tripropylhexylphosphonium chloride with addition of two molar equivalents of $AlCl_3$; 1-butylpyridinium heptachloroaluminate (BPy-$Al_2Cl_7$) was prepared from 1-butylpyridinium chloride with addition of two molar equivalents of $AlCl_3$; 1-hexadecylpyridinium heptachloroaluminate (HDPy-$Al_2Cl_7$) was prepared from 1-hexadecylpyridinium chloride with addition of two molar equivalents of $AlCl_3$; 1-butyl-3-methylimidazolium heptachloroaluminate (BMIM-$Al_2Cl_7$) was prepared from 1-butyl-3-methylimidazolium chloride with addition of two molar equivalents of $AlCl_3$; 1-octylimidazolilum heptachloroaluminate (OMIM-$Al_2Cl_7$) was prepared from 1-octyl-3-methylimidazolium chloride with addition of two molar equivalents of $AlCl_3$; triethylammonium heptachloroaluminate ($Et_3NH$—$Al_2Cl_7$) was prepared from triethylamine hydrochloride with addition of two molar equivalents of $AlCl_3$; triethylammonium heptachloroaluminate with copper additive ($Et_3NH$-$Al_2Cl_7$+0.19 mol CuCl) was prepared from triethylamine hydrochloride with addition of two molar equivalents of $AlCl_3$ and 0.19 molar equivalents of CuCl, and decanted from excess solids; tributylhexylphosphonium bromohexachloroaluminate (TBHP-$Al_2BrCl_6$) was prepared from tributylhexylphosphonium bromide with addition of two molar equivalents of $AlCl_3$; and tributylpentylphosphonium bromohexachloroaluminate (TBPP-$Al_2BrCl_6$) was prepared from tributylpentylphosphonium bromide with addition of two molar equivalents of $AlCl_3$. Aluminum chloride addition was initiated at a temperature between room temperature and 70° C. in order to liquefy the chloride or bromide reactant. When synthesis was conducted on larger scale, it was done in a reactor with a cooling jacket, and the temperature of the exothermic reaction was maintained below 120° C. The kinematic viscosity of each ionic liquid was measured at three temperatures. The Results are shown below in Table 1 and in the FIGURE for a representative sample of each of the ionic liquids. An exponential curve was fit to each set of viscosity measurements and used to determine approximate viscosity at temperatures that were not measured directly.

TABLE 1

Kinematic viscosity of several ionic liquids at various temperatures

| Ionic liquid | Temperature (° C.) | Viscosity (cSt) |
|---|---|---|
| TBHP-$Al_2BrCl_6$ | 23 | 173.7 |
| | 50 | 53.5 |
| | 70 | 27.2 |
| TBPP-$Al_2Cl_7$ | 25 | 86.2 |
| | 50 | 31.86 |
| | 70 | 17.40 |
| TBPP-$Al_2BrCl_6$ | 23 | 112.1 |
| | 50 | 37.07 |
| | 70 | 19.98 |
| TPHP-$Al_2Cl_7$ | 23 | 69.79 |
| | 50 | 25.3 |
| | 70 | 14.30 |
| BMIM-$Al_2Cl_7$ | 23 | 14.95 |
| | 50 | 7.79 |
| | 70 | 5.6 |
| BPy-$Al_2Cl_7$ | 23 | 21.54 |
| | 50 | 8.79 |
| | 70 | 6.0 |
| OMIM-$Al_2Cl_7$ | 23 | 27.28 |
| | 50 | 12.83 |
| | 70 | 8.00 |
| HDPy-$Al_2Cl_7$ | 23 | 119.8 |
| | 50 | 41.83 |
| | 70 | 22.95 |

TABLE 1-continued

Kinematic viscosity of several ionic liquids at various temperatures

| Ionic liquid | Temperature (° C.) | Viscosity (cSt) |
|---|---|---|
| TBHP-Al$_2$Cl$_7$ | 25 | 111.1 |
| | 50 | 39.14 |
| | 70 | 22.02 |
| TBMP-Al$_2$Cl$_7$ | 25 | 55.41 |
| | 50 | 22.34 |
| | 70 | 12.74 |
| Et$_3$NH—Al$_2$Cl$_7$ | 25 | 16.36 |
| | 50 | 8.32 |
| | 70 | 5.56 |
| Et$_3$NH—Al$_2$Cl$_7$ + 0.19 mol CuCl | 25 | 18.43 |
| | 50 | 9.279 |
| | 70 | 6.092 |

Example 2

Alkylation Testing

Four types of ionic liquids, TBHP-Al$_2$Cl$_7$, TBPP-Al$_2$Cl$_7$, TBMP-Al$_2$Cl$_7$, BMIM-Al$_2$Cl$_7$ were prepared according to the procedures in example 1. Caprolactamium Al$_2$Cl$_7$ (CPL-Al$_2$Cl$_7$) was prepared as described in U.S. application Ser. No. 14/271,308 filed May 6, 2014. The ionic liquids were each tested as catalysts for isobutane alkylation with 2-butenes. The conditions of each run are found in Tables 2-7. Ionic liquid was loaded in a 300 cc autoclave (the amount is specified for each experiment in the table) with an amount of 2-chlorobutane (used as a catalyst promoter). The autoclave was fitted with a 1.25" diameter Cowles-type impeller. 80 g of isobutane was charged into the autoclave and the reactor was pressurized with nitrogen to about 3.4 MPa(g) (500 psig). After pressurizing the reactor, the mixture was stirred at 1700-1900 RPM for 20 minutes to ensure breakdown of 2-chlorobutane. The reactor was heated to the desired temperature, mixing at 1700 to 1900 RPM was resumed, and the reaction was initiated by the addition of approximately 8 g of 2-butenes (mixed cis- and trans-isomers), over the course of the specified olefin addition time specified. The 2-butenes blend also contained about 8 wt % n-pentane that was used as a tracer to verify the amount of butenes added. Mixing was stopped immediately after the olefin addition time, and the mixture was allowed to settle. The hydrocarbon was analyzed by gas chromatography (GC). Some experiments were repeated several times, and in some cases with different batches of the same ionic liquid. In many cases, the amount of 2-chlorobutane was adjusted in repeat experiments until the optimal C$_8$ selectivity and greater than 99% conversion was obtained. Tables 2-7 also shows results for these experiments. The calculation of selectivity for C$_5$, C$_6$, C$_7$, and C$_{9+}$ is similar to that for C$_8$ selectivity.

TABLE 2

| IL | BMIM** | BMIM | BMIM | BMIM | BMIM | BMIM |
|---|---|---|---|---|---|---|
| IL loading g | 8 | 8 | 8 | 8 | 4 | 4 |
| g of C$_4$= fed | 7.14 | 8.04 | 7.82 | 6.91 | 7.91 | 6.94 |
| End of run IL volume % | 3.8% | 3.8% | 3.8% | 3.8% | 1.9% | 1.9% |
| 2-Chlorobutane g | 0.23 | 0.40 | 0.503 | 0.496 | 0.252 | 0.402 |
| Actual i/o (mol/mol) | 10.7 | 9.6 | 9.9 | 11.20 | 9.76 | 11.13 |
| Olefin addition time min | 2.5 | 2.5 | 2.5 | 8 | 8 | 8 |
| Olefin:2-chlorobutane mole ratio | 50.57 | 33.08 | 25.64 | 22.98 | 51.82 | 28.50 |
| Temp ° C. | 25 | 25 | 25 | 25 | 25 | 25 |
| Kinematic viscosity of IL at 25° C. | 15.00 | 13.98 | 13.98 | 13.98 | 13.98 | 13.98 |
| Olefin feed rate mol/mol IL/hr | 168.5 | 189.8 | 184.5 | 51.0 | 116.7 | 102 |
| Butenes Conversion % | 100.00 | 99.94 | 99.95 | 99.44 | 56.41 | 99.96 |
| RONC (research octane number calculated) | 95.53 | 94.93 | 94.56 | 92.94 | 91.71 | 96.18 |
| Yld, g C$_5$+/g C$_4$= | 2.15 | 2.18 | 2.15 | 2.11 | 1.29 | 2.15 |
| TMP/DMH | 11.64 | 11.10 | 10.33 | 7.39 | 17.34 | 13.30 |
| % Sel. C$_5$s | 6.02 | 6.80 | 7.70 | 8.15 | 5.63 | 4.80 |
| % Sel. C$_6$s | 4.50 | 5.07 | 5.32 | 4.99 | 5.06 | 4.17 |
| % Sel. C$_7$s | 4.14 | 3.88 | 4.46 | 3.86 | 3.98 | 3.41 |
| % Sel. C$_8$s | 78.26 | 75.52 | 73.48 | 76.53 | 54.63 | 81.61 |
| % Sel. C$_9$+ s | 7.08 | 8.73 | 9.03 | 6.47 | 30.71 | 6.01 |
| % Sel. C$_5$-C$_7$s | 14.66 | 15.75 | 17.49 | 17.00 | 14.67 | 12.38 |

*This run used a different batch of IL and a 1" diameter impeller

TABLE 3

| IL | TBMP | TBMP | TBMP | TBMP | TBMP | TBMP |
|---|---|---|---|---|---|---|
| IL loading g | 8 | 8 | 8 | 4 | 4 | 4 |
| g of C$_4$= fed | 7.87 | 7.15 | 6.67 | 6.58 | 7.58 | 7.5 |
| End of run IL volume % | 4.2% | 4.2% | 4.3% | 2.2% | 2.2% | 2.2% |
| 2-Chlorobutane g | 0.375 | 0.375 | 0.422 | 0.188 | 0.189 | 0.187 |
| Actual i/o (mol/mol) | 10.2 | 11.2 | 11.88 | 12.1 | 10.2 | 10.3 |
| Olefin addition time min | 2.5 | 2.5 | 8 | 5 | 6.5 | 8 |
| Olefin:2-chlorobutane mole ratio | 34.63 | 31.45 | 26.06 | 57.79 | 66.14 | 66.08 |
| Temp ° C. | 25 | 25 | 25 | 25 | 25 | 25 |
| Kinematic viscosity of IL at 25° C. | 56.8 | 56.8 | 55.41 | 56.8 | 56.8 | 56.8 |
| Olefin feed rate mol/mol IL/hr | 219 | 199 | 58 | 183 | 162 | 130 |
| Butenes Conversion % | 99.6 | 99.9 | 99.92 | 90.1 | 91.3 | 99.8 |
| RONC | 95.0 | 95.2 | 94.69 | 95.7 | 95.1 | 96.1 |
| Yld, g C$_5$+/g C$_4$= | 2.14 | 2.34 | 2.20 | 2.13 | 1.97 | 2.2 |
| TMP/DMH | 11.3 | 12.5 | 9.33 | 17.7 | 18.3 | 16.3 |
| % Sel. C$_5$s | 7.5 | 7.0 | 6.08 | 5.3 | 4.9 | 4.9 |

TABLE 3-continued

| IL | TBMP | TBMP | TBMP | TBMP | TBMP | TBMP |
|---|---|---|---|---|---|---|
| % Sel. $C_6$s | 4.5 | 4.8 | 4.22 | 5.4 | 5.5 | 4.8 |
| % Sel. $C_7$s | 4.5 | 4.4 | 3.98 | 4.6 | 4.2 | 4.4 |
| % Sel. $C_8$s | 74.3 | 74.5 | 77.72 | 71.8 | 68.3 | 76.0 |
| % Sel. $C_9$+ s | 9.2 | 9.3 | 8.00 | 12.9 | 17.1 | 9.9 |
| % Sel. $C_5$-$C_7$s | 16.5 | 16.2 | 14.28 | 15.3 | 14.6 | 14.1 |

TABLE 4A

| IL | TBPP | TBPP | TBPP | TBPP | TBPP |
|---|---|---|---|---|---|
| IL loading g | 8 | 8 | 8 | 8 | 8 |
| g of $C_4$= fed | 6.99 | 6.81713 | 8.17217 | 8.1714 | 7.93 |
| End of run IL volume % | 4.3% | 4.4% | 4.3% | 4.3% | 4.3% |
| 2-Chlorobutane g | 0.329 | 0.499 | 0.503 | 0.42 | 0.34 |
| Actual i/o (mol/mol) | 11 | 11.6 | 9.4 | 9.5 | 9.7 |
| Olefin addition time min | 2.5 | 2.5 | 2.5 | 2.5 | 8 |
| Olefin:2-chlorobutane mole ratio | 35.05 | 22.54 | 26.81 | 32.10 | 38.49 |
| Temp ° C. | 25 | 25 | 25 | 25 | 25 |
| Kinematic viscosity of IL at 25° C. | 86.2 | 86.8 | 83.8 | 83.8 | 86.2 |
| Olefin feed rate mol/mol IL/hr | 215 | 210 | 252 | 252 | 76 |
| Butenes Conversion % | 99.98 | 99.93 | 99.88 | 99.93 | 99.94 |
| RONC | 95.61 | 95.22 | 95.65 | 94.84 | 94.46 |
| Yldg $C_5$+/g $C_4$= | 2.18 | 2.16 | 2.13 | 2.17 | 2.13 |
| TMP/DMH | 16.37 | 12.96 | 16.02 | 11.78 | 9.49 |
| % Sel. $C_5$s | 5.83 | 6.77 | 6.18 | 7.63 | 7.67 |
| % Sel. $C_6$s | 5.53 | 5.88 | 6.16 | 6.03 | 5.30 |
| % Sel. $C_7$s | 4.66 | 5.13 | 5.12 | 5.18 | 4.75 |
| % Sel. $C_8$s | 72.36 | 71.98 | 71.77 | 70.86 | 73.81 |
| % Sel. $C_9$+ s | 11.62 | 10.25 | 10.77 | 10.30 | 8.47 |
| % Sel. $C_5$-$C_7$s | 16.02 | 17.78 | 17.46 | 18.84 | 17.72 |

TABLE 4B

| IL | TBPP | TBPP | TBPP | TBPP | TBPP |
|---|---|---|---|---|---|
| IL loading g | 6 | 6 | 4 | 4 | 4 |
| g of $C_4$= fed | 7.89 | 7.25 | 7.42 | 7.76 | 7.91 |
| End of run IL volume % | 3.3% | 3.3% | 2.2% | 2.4% | 2.2% |
| 2-Chlorobutane g | 0.259 | 0.342 | 0.163 | 0.381 | 0.43 |
| Actual i/o | 9.8 | 10.7 | 10.4 | 10.0 | 9.8 |
| Olefin addition time min | 8 | 8 | 8 | 8 | 8 |
| Olefin:2-chlorobutane | 50.23 | 34.99 | 75.11 | 33.59 | 30.35 |
| Temp ° C. | 25 | 25 | 25 | 25 | 25 |
| Kinematic viscosity of IL at 25° C. | 86.2 | 86.2 | 86.2 | 86.2 | 86.2 |
| Olefin feed rate mol/mol IL/hr | 101 | 93 | 143 | 149 | 152 |
| Butenes Conversion % | 53.38 | 99.47 | 30.21 | 95.37 | 99.90 |
| RONC | 95.04 | 96.46 | 90.30 | 93.77 | 94.82 |
| Yld g $C_5$+/g $C_4$= | 1.77 | 2.12 | 1.50 | 1.80 | 2.01 |
| TMP/DMH | 19.52 | 16.88 | 13.60 | 20.46 | 22.64 |
| % Sel. $C_5$s | 4.77 | 4.74 | 6.39 | 5.13 | 5.06 |
| % Sel. $C_6$s | 4.37 | 4.81 | 4.28 | 6.94 | 7.19 |
| % Sel. $C_7$s | 4.63 | 4.00 | 5.01 | 5.17 | 5.31 |
| % Sel. $C_8$s | 69.85 | 78.19 | 52.52 | 58.85 | 63.60 |
| % Sel. $C_9$+ s | 16.38 | 8.25 | 31.80 | 23.92 | 18.83 |
| % Sel. $C_5$-$C_7$s | 13.77 | 13.56 | 15.68 | 17.23 | 17.57 |

TABLE 5

| IL | TBPP | TBPP | TBPP | TBPP | TBPP |
|---|---|---|---|---|---|
| IL loading g | 8 | 8 | 6 | 6 | 8 |
| g of $C_4$= fed | 6.83 | 7.24 | 7.59 | 6.82 | 8.04 |

TABLE 5-continued

| IL | TBPP | TBPP | TBPP | TBPP | TBPP |
|---|---|---|---|---|---|
| End of run IL volume % | 4.4% | 4.3% | 3.3% | 3.3% | 4.3% |
| 2-Chlorobutane g | 0.329 | 0.329 | 0.329 | 0.33 | 0.55 |
| Actual i/o (mol/mol) | 11.30 | 10.4 | 10.2 | 11.2 | 9.6 |
| Olefin addition time min | 2.5 | 2.5 | 8 | 4 | 4 |
| Olefin:2-chlorobutane mole ratio | 34.25 | 36.32 | 38.05 | 34.10 | 24.13 |
| Temp ° C. | 38 | 38 | 38 | 38 | 38 |
| Kinematic viscosity of IL at 25° C. | 86.2 | 86.2 | 86.2 | 86.2 | 86.2 |
| Olefin feed rate mol/mol IL/hr | 209.0 | 222.9 | 97.3 | 174.8 | 154.7 |
| Butenes Conversion % | 99.49 | 99.95 | 99.92 | 53.01 | 99.61 |
| RONC | 94.58 | 94.45 | 93.60 | 92.79 | 93.95 |
| Yld g $C_5$+/g $C_4$= | 2.19 | 2.09 | 2.16 | 1.86 | 2.20 |
| TMP/DMH | 12.18 | 11.12 | 7.85 | 14.60 | 9.61 |
| % Sel. $C_5$s | 7.62 | 8.16 | 8.62 | 6.30 | 8.11 |
| % Sel. $C_6$s | 6.44 | 6.43 | 5.79 | 6.42 | 6.15 |
| % Sel. $C_7$s | 6.29 | 6.26 | 5.69 | 6.13 | 6.83 |
| % Sel. $C_8$s | 66.42 | 68.03 | 70.57 | 61.40 | 67.99 |
| % Sel. $C_9$+ s | 13.22 | 11.12 | 9.34 | 19.75 | 10.92 |
| % Sel. $C_5$-$C_7$s | 20.35 | 20.84 | 20.09 | 18.85 | 21.09 |

TABLE 6

| IL | TBHP | TBHP | TBHP | TBHP |
|---|---|---|---|---|
| IL loading g | 8 | 8 | 8 | 8 |
| g of $C_4$= fed | 6.85 | 6.48 | 7.65 | 7.67 |
| End of run Calculated IL volume % | 4.4% | 4.4% | 4.4% | 4.4% |
| 2-Chlorobutane g | 0.242 | 0.26 | 0.66 | 0.438 |
| Actual i/o (mol/mol) | 11.7 | 12.3 | 10.1 | 10.4 |
| Olefin addition time min | 2.5 | 2.5 | 2.5 | 8 |
| Olefin:2-chlorobutane mole ratio | 46.71 | 41.13 | 19.12 | 28.88 |
| Temp ° C. | 25 | 25 | 25 | 25 |
| Kinematic viscosity of IL at 25° C. | 111.1 | 111.1 | 108.4 | 111.1 |
| Olefin feed rate mol/mol IL/hr | 216 | 204 | 241 | 76 |
| Butenes Conversion % | 99.9 | 100.0 | 99.96 | 99.9 |
| RONC | 95.0 | 94.5 | 94.74 | 96.0 |
| Yld-1, g $C_5$+/g $C_4$= based on $nC_5$ | 2.1 | 2.2 | 2.09 | 2.1 |
| TMP/DMH | 17.5 | 11.4 | 16.38 | 14.8 |
| % Sel. $C_5$s | 6.0 | 7.1 | 6.08 | 5.4 |
| % Sel. $C_6$s | 7.1 | 6.4 | 7.15 | 5.0 |
| % Sel. $C_7$s | 5.6 | 5.5 | 5.41 | 4.5 |
| % Sel. $C_8$s | 65.8 | 68.5 | 66.60 | 76.7 |
| % Sel. $C_9$+ s | 15.5 | 12.5 | 14.77 | 8.5 |
| % Sel. $C_5$-$C_7$s | 18.7 | 19.0 | 18.63 | 14.9 |

TABLE 7

| IL | CPL | CPL |
|---|---|---|
| IL loading g | 3.79 | 6.21 |
| g of $C_4$= fed | 8.77 | 3.09 |
| End of run IL volume % | 1.80% | 6.78% |
| 2-Chlorobutane g | 0.338 | 0.548 |
| Actual i/o (mol/mol) | 8.91 | 10.63 |
| Olefin addition time min | 8 | 2 |
| Olefin:2-chlorobutane mole ratio | 42.74 | 9.29 |
| Temp ° C. | 25 | 25 |

TABLE 7-continued

| IL | CPL | CPL |
|---|---|---|
| Kinematic viscosity of IL at 25° C. | 205.1 | 205.1 |
| Olefin feed rate mol/mol IL/hr | 120.33 | 103.4 |
| Butenes Conversion % | 99.92 | 99.94 |
| RONC | 95.42 | 93.81 |
| Yld g $C_5$+/g $C_4$= | 2.13 | 2.18 |
| TMP/DMH | 15.94 | 9.74 |
| % Sel. $C_5$s | 6.14 | 7.61 |
| % Sel. $C_6$s | 5.75 | 6.1 |
| % Sel. $C_7$s | 4.64 | 4.29 |
| % Sel. $C_8$s | 73.26 | 73.11 |
| % Sel. $C_9$+ s | 10.2 | 8.89 |
| % Sel. $C_5$-$C_7$s | 16.53 | 17.99 |

As used herein, the term about means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed:

1. An alkylation process comprising:
 passing an isoparaffin having from 4 to 10 carbon atoms and an olefin having from 3 to 10 carbon atoms to an alkylation reactor containing an unsupported, halometallate based ionic liquid catalyst to generate an alkylate having a research octane number of at least about 93, wherein the alkylation reactor is operated at reaction conditions comprising an operating temperature greater than about 20° C., a molar ratio of isoparaffin to olefin of less than about 20:1, an overall olefin feed rate of greater than about 30 mol olefin/mol ionic liquid catalyst/hr, a total residence time in a range of about 1 min to about 30 min, and less than about 10 vol % of the halometallate based ionic liquid catalyst.

2. The process of claim 1 wherein the halometallate based ionic liquid catalyst has a viscosity of less than about 120 cSt at a temperature of 25° C., and wherein there is less than about 5 vol % of the halometallate based ionic liquid catalyst.

3. The process of claim 1 wherein the halometallate based ionic liquid catalyst has a viscosity of less than about 100 cSt at a temperature of 25° C., and wherein there is less than about 4 vol % of the halometallate based ionic liquid catalyst.

4. The process of claim 1 wherein the halometallate based ionic liquid catalyst has a viscosity of less than about 60 cSt at a temperature of 25° C., and wherein there is less than about 3 vol % of the halometallate based ionic liquid catalyst.

5. The process of claim 1 wherein there is less than about 5 vol % of the halometallate based ionic liquid catalyst, and wherein the total residence time is the range of about 2 min to about 10 min.

6. The process of claim 1 wherein there is less than about 4 vol % of the haloaluminate based ionic liquid catalyst, and wherein the total residence time is the range of about 3 min to about 30 min.

7. The process of claim 1 wherein there is less than about 3 vol % of the haloaluminate based ionic liquid catalyst, and wherein the total residence time is the range of about 4 min to about 30 min.

8. The process of claim 1 wherein the isoparaffin has 4 carbon atoms and the olefin has 4 carbon atoms, the alkylation process has a selectivity for $C_8$ of at least about 70%, and the alkylate has a mole ratio of trimethylpentane to dimethylhexane of greater than 12.

9. The process of claim 1 wherein an olefin conversion is at least about 96%.

10. The process of claim 1 further comprising adding an acid promoter to the alkylation reactor.

11. The process of claim 10 wherein a molar ratio of olefin to acid promoter of greater than about 15:1.

12. The process of claim 1 wherein the halometallate based ionic liquid catalyst comprises a phosphonium based ionic liquid, an imidazolium based ionic liquid, a pyridinium based ionic liquid, a pyrrolidinium based ionic liquid, a pyrrolidonium based ionic liquid, or a lactamium based ionic liquid.

13. The process of claim 1 wherein the halometallate based ionic liquid catalyst comprises tripropylpentylphosphonium heptachloroaluminate, tripropylhexylphosphonium heptachloroaluminate, tributylpentylphosphonium heptachloroaluminate, tributylhexylphosphonium heptachloroaluminate, tributylmethylphosphonium heptachloroaluminate, 1-butyl-3-methyl imidizolium heptachloroaluminate, 1-ethyl-3-methylimidazolium heptachloroaluminate, 1-butylpyridinium heptachloroaluminate, 1-butyl-2-methyl-pyridinium heptachloroaluminate, 1-butyl-3-methyl-pyridinium heptachloroaluminate, 1-butyl-4-methyl-pyridinium heptachloroaluminate, 1-ethyl-1-methylpyrrolidinium heptachloroaluminate, 1-butyl-1-methylpyrrolidinium heptachloroaluminate, caprolactamium heptachloroaluminate, N-methylcaprolactamium heptachloroaluminate, N-methylpyrrolidonium heptachloroaluminate, pyrrolidonium heptachloroaluminate, δ-valerolactamium heptachloroaluminate, N-methyl-δ-valerolactamium heptachloroaluminate or combinations thereof.

14. An alkylation process comprising:
 passing an isoparaffin having from 4 carbon atoms and an olefin having 4 carbon atoms to an alkylation reactor containing an unsupported, halometallate based ionic liquid catalyst to generate an alkylate having a research octane number of at least about 93,
 wherein the alkylation reactor is operated at reaction conditions comprising an operating temperature greater than about 20° C., a molar ratio of isoparaffin to olefin of less than about 20:1, an overall olefin feed rate of greater than about 30 mol olefin/mol ionic liquid catalyst/hr, a total residence time in a range of about 1 min to about 30 min, and less than about 10 vol % of the halometallate based ionic liquid catalyst,
 wherein the haloaluminate based ionic liquid catalyst comprises a phosphonium based ionic liquid, an imidazolium based ionic liquid, a pyridinium based ionic liquid, or a lactamium based ionic liquid, and
 wherein an olefin conversion is at least about 96%.

15. The process of claim 14 wherein the haloaluminate based ionic liquid has a viscosity of less than about 120 cSt at a temperature of 25° C., and wherein there is less than about 5 vol % of the ionic liquid catalyst.

16. The process of claim 14 wherein there is less than about 5 vol % of the halometallate based ionic liquid catalyst, and wherein the total residence time is the range of about 2 min to about 10 min.

17. The process of claim 14 wherein there is less than about 4 vol % of the haloaluminate based ionic liquid, and wherein the total residence time is the range of about 3 min to about 30 min.

18. The process of claim 14 wherein the research octane number is at least about 95, the reaction has a selectivity for $C_8$ of at least about 70%, and/or the alkylate has a mole ratio of trimethylpentane to dimethylhexane of greater than 12.

19. The process of claim 14 wherein the ionic liquid catalyst comprises tripropylpentylphosphonium heptachloroaluminate, tripropylhexylphosphonium heptachloroaluminate, tributylpentylphosphonium heptachloroaluminate, tributylhexylphosphonium heptachloroaluminate, tributylmethylphosphonium heptachloroaluminate, 1-butyl-3-methyl imidizolium heptachloroaluminate, 1-ethyl-3-methylimidazolium heptachloroaluminate, 1-butylpyridinium heptachloroaluminate, 1-butyl-2-methyl-pyridinium heptachloroaluminate, 1-butyl-3-methyl-pyridinium heptachloroaluminate, 1-butyl-4-methyl-pyridinium heptachloroaluminate, 1-ethyl-1-methylpyrrolidinium heptachloroaluminate, 1-butyl-1-methylpyrrolidinium heptachloroaluminate, caprolactamium heptachloroaluminate, N-methylcaprolactamium heptachloroaluminate, N-methylpyrrolidonium heptachloroaluminate, pyrrolidonium heptachloroaluminate, δ-valerolactamium heptachloroaluminate, N-methyl-δ-valerolactamium heptachloroaluminates, or combinations thereof.

* * * * *